United States Patent [19]

Pasarela et al.

[11] 4,289,525

[45] Sep. 15, 1981

[54] SOLID COMPOSITIONS OF A PYRAZOLIUM SALT, UREA AND A LIQUID SURFACTANT

[75] Inventors: Nunzio R. Pasarela, Bridgewater; Choong-Gook Jang, Princeton, both of N.J.

[73] Assignee: American Cyanamid Co., Stamford, Conn.

[21] Appl. No.: 58,711

[22] Filed: Jul. 18, 1979

[51] Int. Cl.³ .............................................. A01N 43/56
[52] U.S. Cl. ................................... 71/92; 71/DIG. 1
[58] Field of Search ............................. 71/92, DIG. 1

[56] References Cited

U.S. PATENT DOCUMENTS 3,154,397 10/1964 Martin .................................. 71/113
3,922,161 11/1975 Walworth et al. ..................... 71/92

*Primary Examiner*—Catherine L. Mills
*Attorney, Agent, or Firm*—H. G. Jackson

[57] ABSTRACT

There are provided solid herbicidal compositions comprising a molecular solution of a liquid, non-ionic surfactant, a 1,2-dimethyl-3,5-diphenylpyrazolium salt and urea in one another. There is also provided a method for preparing said compositions which comprises the steps of melting together the components of the composition at elevated temperatures and then cooling said melt.

6 Claims, No Drawings

SOLID COMPOSITIONS OF A PYRAZOLIUM SALT, UREA AND A LIQUID SURFACTANT

The present invention relates to a solid, three component herbicidal composition comprising a molecular solution of a liquid, non-ionic surfactant, such as octylhenoxy polyethoxy ethanol, or nonylphenoxy polyethoxy ethanol, a 1,2-dimethyl-3,5-diphenylpyrazolium salt and urea, in one another. The invention further relates to a method for preparing the aforementioned ternary composition which comprises melting the components of same together, and then cooling said melt.

As it is known, 1,2-dimethyl-3,5-diphenylpyrazolium salts can be formulated as concentrated aqueous solutions useful as herbicidal compositions. Unfortunately, such solutions of 1,2-dimethyl-3,5-diphenylpyrazolium salts, especially the methylsulfate, tend to deposit some of the herbicide in a crystalline form when stored for a period of time, especially when exposed to a cold environment. Once partial crystallization has occurred, such concentrates have to be heated and agitated in order to redissolve the deposited solids before they can be used for the preparation of dilute aqueous sprays. Similarly, conventional solid compositions containing said pyrazolium toxicants and the desired surfactants usually result in soft, and at times, oily products with poor flow properties which are not entirely suitable for agricultural use.

In general, the above solid herbicide-urea-surfactant compositions which are characterized as free flowing powders and soluble in water, can be prepared in a straightforward manner as hereinbelow set forth.

A suitable surfactant, namely, octylphenoxy polyethoxy ethanol, or nonyl-phenoxy polyethoxy ethanol, is heated to 90° C. or above. To the latter are next added the herbicide, 1,2-dimethyl-3,5-diphenylpyrazolium salt, preferably the methylsulfate, and urea, and the mixture stirred and heated until a homogeneous solution is obtained. The molten mixture is then poured or sprayed on a cold surface, where it rapidly congeals. If so desired, the above molten mixture may be sprayed into a cold, gaseous environment, wherein the individual droplets of said spray congeal while in free flight, and are collected as a fine powder. The solidified composition is quite hard and has an amorphous, sometimes crystalline appearance. In this state, the above compositions may be converted to granules, beads, prills, flakes and the like, with commercially available equipment. Alternatively, the above, molten mixture may be extruded into various shapes by commercially available hot-melt extruders.

Advantageously, the sequence steps of heating, mixing and melting the components of the hereinabove described compositions together are not critical. Thus, equally good results may be obtained by melting the herbicidal salt or the urea first, and then adding the remaining components in any order desired, followed by stirring and heating the thus obtained mix until a homogeneous melt is obtained.

The solid particles of the herbicide urea composition obtained by the above process are free-flowing, dry and relatively non-hygroscopic. These compositions, especially when particulated, are readily soluble in cold water. An additional advantage of the present compositions is that the particles shaped therefrom, when packed in containers do not form lumps or cake-up upon storage.

Flowability of the above particles of said compositions may be further increased by coating said particles with about 1% to 5%, by weight, and preferably from 1% to 3%, by weight, of a solid lubricating agent, such as a fumed synthetic silica or a precipitated silica with a particle-size range of between 0.015 microns and 2 microns.

The liquid, non-ionic surfactant, referred to hereinabove as "octylphenoxy polyethoxy ethanol" has an average molecular weight of 628 and contains an average of 9 to 10 ethylene oxide units, representing 67%, by weight, of said surfactant. The specific gravity of this surfactant is 1.065 at 25° C.; the viscosity is 240 cps at 25° C. (Brookfield; 12 r.p.m.), and the flash point is >300° F. (TOC). While the liquid non-ionic surfactant, referred to as "nonylphenoxy polyethoxy ethanol" contains an average of 9 ethylene oxide units, representing 66% by weight of said surfactant, the specific gravity of this surfactant is 1.06 at 25° C., the viscosity is 224–300 cps at 25° C., and the flash point is >200° F.

In practice, dilute aqueous sprays of the above compositions are used to control undesirable weed species in the presence of agronomic crops.

Alternatively, the compositions of the present invention may be prepared as follows: from about 10% to about 30%, by weight, and, preferably, from 13% to 27%, by weight, (of the composition) of octylphenoxy polyethoxy ethanol is heated to a temperature range of from about 90° C. to about 160° C. and, preferably, from 125° C. to 128° C. To the above heated surfactant is added from about 33% to 64%, by weight, of 1,2-dimethyl-3,5-diphenylpyrazolium methylsulfate, and from about 4% to about 57%, by weight, and, preferably, from 9% to 54%, by weight, of urea to adjust the overall composition to 100%, by weight. After the addition is completed, the resultant mixture is stirred and heated at the temperature range specified above, for a period of time sufficient to obtain a homogeneous melt, usually from about 0.5 hour to about 5 hours. Resultant melt may be used directly in a hot-melt extruder to form various shapes, or may be poured or sprayed on a cold surface where it congeals. The melt may be sprayed into a cold gaseous environment, wherein the individual droplets of said spray congeal while in free flight. The thus-obtained solid may then be formed, if desired, into flakes, granules, beads, prills and the like, by commercially available equipment. The present composition in its final shape is free-flowing, dry and essentially nonhygroscopic. The flowability of the above particles of said composition may further be improved by coating same with about 1% to 5%, by weight, and, preferably, from about 1% to 3%, by weight, of a solid lubricating agent, such as a fumed synthetic silica or a precipitated silica having a particle-size range of from 0.015 micron to 2 microns.

The above-described solid compositions may also be prepared by pre-blending all components of said composition at room temperature and then subjecting said blend to the above melt-cool process.

The 1,2-dimethyl-3,5-diphenylpyrazolium salts of the present compositions are known. For instance, they have been disclosed in U.S. Pat. No. 3,882,142, issued on May 6, 1975 to Walworth et al. Their use as herbicides has been disclosed in U.S. Pat. No. 3,922,161, issued on Nov. 25, 1975 to Walworth et al.

The hereinabove-defined compositions are eminently suitable for the postemergence control of undesired plant species, especially wild oats in the presence of crops such as wheat, barley, and rye, when applied at a rate of from 0.56 to 3.36 kg per hectare of active cation.

The present invention is further illustrated by the following examples.

EXAMPLE 1

Preparation of a solid composition consisting of a pyrazolium herbicide, a surfactant and urea Octylphenoxy polyethoxy ethanol (367.74 g; 27% by weight of composition) is heated to 150° C., then 1,2-dimethyl-3,5-diphenylpyrazolium methylsulfate (871.68 g; 64% by weight of composition) is added in small increments with stirring, and then the mixture stirred at 150°–158° C. until a clear solution occurs. Next, urea (122.58 g; 9.0% by weight of composition) is added and stirring of the mixture continues until a homogeneous melt is formed. The molten mixture is poured into aluminum pans and allowed to solidify.

A portion of the solidified product is ground in a micropulverizer, while another portion of the product is coarsely ground to pass through a 10 mesh screen. Samples of both are stored at 55° C. for 3 days, after which neither sample shows visible physical changes in appearance, flowability and solubility.

The freshly prepared composition contains 63.46% by weight of 1,2-dimethyl-3,5-diphenylpyrazolium methylsulfate. A sample stored at 45° C. for one month assays 63.46% by weight, and a sample stored at 45° C. for two month assays 62.91%, by weight, of the above herbicide.

EXAMPLE 2

Evaluation of the effect of the temperature of melting on the herbicide-surfactant-urea composition A. Octylphenoxy polyethoxy ethanol (492 g; 24.6% by weight of composition) is heated to 140° C. and 1,2-dimethyl-3,5-diphenylpyrazolium methylsulfate (1308 g; 65.4% by weight of composition) is added at once. Next, urea (200 g; 10% by weight of composition) is added and the mixture heated at 140°–155° C. for 4 hours with intermittent stirring. Resultant solution (2000 g) is poured into an aluminum cooling pan, and when solidified, is ground. The composition contains 63.81%, by weight, of 1,2-dimethyl-3,5-diphenylpyrazolium methylsulfate.

B. The preparation under A is repeated, except that the sample is heated at 160°–170° C. for 4 hours. On cooling in the aluminum pan a few crystals form in the composition, but the bulk of it remains a tarry, tacky mass. The material is not analyzed.

C. Octylphenoxy polyethoxy ethanol (369 g; 24.58% by weight of composition) is heated to 90° C., then 1,2-dimethyl-3,5-diphenylpyrazolium methylsulfate (491 g) is added and the whole stirred until a thin slurry is obtained. Next, urea (150 g; 10% by weight of composition) is added, the temperature of the mixture raised to 120° C. and then a second portion of 1,2-dimethyl-3,5-diphenylpyrazolium methylsulfate (491 g; a total of 982 g; 65.42% by weight of composition is used) is added and the whole heated at 125°–128° C. for 5 hours. A sample removed from the melt approximately 30 minutes after start analyses for 64.62%, by weight, of 1,2-dimethyl-3,5-diphenylpyrazolium methylsulfate, while the rest of the preparation assays 64.76%.

A sample (43 g) is spread out on a large petri dish and exposed to the environment (with daily variations in ambient temperature and relative humidity). The sample shows a 0.9 g (2.1%) weight gain in 10 days.

EXAMPLE 3

Preparation of a herbicide-fertilizer-surfactant composition

Octylphenoxy polyethoxy ethanol (52.8 g; 13.2% by weight of formulation) is heated to 155° C., then 1,2-dimethyl-3,5-diphenylpyrazolium methylsulfate (133.6 g; 33.4% by weight of formulation) is added slowly and the mixture stirred until a clear solution occurs. Next, urea (213.6 g; 53.4% by weight of formulation) is added and the mixture stirred until a homogeneous melt is formed. The melt is poured into an aluminum cooling pan, and when solidified is ground to 10 mesh.

EXAMPLE 4

Preparation of a flaked herbicide-surfactant-urea composition

A 45.36 kg (100 lbs) batch of a composition comprising: 65.4% by weight of 1,2-dimethyl-3,5-diphenylpyrazolium methyl sulfate (98%), 24.6% by weight of octylphenoxy polyethoxy ethanol and 10.0% by weight of urea is prepared by method C for Example 2 and loaded into the heated reservoir of a rotating drum type of flaking machine. While in the reservoir the batch is kept fluid by maintaining its temperature at about 110° C.

A slowly rotating heated drum (6 r.p.m; 45°–48° C.) continuously picks up on its surface a film of the above molten composition from the reservoir (a flat pan). The thickness of the film is then adjusted with a pinch roller from about 0.79 mm. to about 1.58 mm (1/32″ to 1/16″). The slowly solidifying, but still pliable film of composition, is then shaved off from the drum with a doctor blade, and falls into a storage bin. While in free flight, the material cools off and fully solidifies, and fractures into individual flakes, partially while still in flight and partially upon impacting in the storage bin.

The above described composition of Example 4 can also be flaked by using a commercially available steel belt flaking-cooling machine.

EXAMPLE 5

Preparation of a pan granular formulation of a herbicide-surfactant-urea composition Employing the molten composition of Example 4, granulation is attained by using a pan granulation (agglomeration) machine, such as the HOT MELT GRANULATION™ equipment manufactured by FERRO-TECH Company of Detroit, Mich.

EXAMPLE 6

Postemergence Herbicidal Activity

The postemergence herbicidal activity of the composition of the present invention is demonstrated by the following tests, wherein wild oats are treated with compositions both of a conventional formulation and the formulation of Example 1, in the presence of wheat and barley. In the tests, seedling plants are grown in separate cups for about two weeks. The test formulations are dissolved in water in sufficient quantity to provide the equivalent of about 0.125 kg to 4.0 kg per hectare of active cation when applied to the plants through a spray nozzle operating at 2.81 kg/cm² pressure for a predetermined time. After spraying, the plants are placed on greenhouse benches and are cared for in the usual manner, commensurate with conventional greenhouse practices. Five weeks after treatment, the seedling plants are examined and rated according to the rating system provided below. The data obtained are reported in Table I below.

TABLE I

RATING SYSTEM

| RATING | % CONTROL (COMPARED TO CHECK) |
| --- | --- |
| 9 - Complete kill | 100 |
| 8 - Approaching complete kill | 91–99 |
| 7 - Good herbicidal effect | 80–90 |
| 6 - Herbicidal effect | 65–79 |
| 5 - Definite injury | 45–64 |
| 4 - Injury | 30–44 |
| 3 - Moderate effect | 10–29 |
| 2 - Slight effect | 6–15 |
| 1 - Trace effect | 1–5 |
| 0 - No effect | 0 |

The above rating scale is based upon visual observation of plant stand, vigor, malformation, size, chlorosis, and overall plant appearance as compared with a control.

| | Plant Species | |
| --- | --- | --- |
| WO | = Wild oat | (*Avena Fatua*) |
| E | = Wheat, Era | (*Triticum aestivum* c.v. Era) |
| W | = Wheat, Waldron | (*Triticum aestivum* c.v. Waldron) |
| BY | = Barley, Steptoe | (*Hordeum vulgare*) |

TABLE I

Evaluation of the postemergence wild oat herbicidal activity of the invention, as compared to conventional formulations.

| Rate kg/ha | Conventional formulation | | | | 64% real, Composition of Ex. 1 | | | | 32% real, Composition of Ex. 1 | | | |
| --- | --- | --- | --- | --- | --- | --- | --- | --- | --- | --- | --- | --- |
| | WO | E | W | BY | WO | E | W | BY | WO | E | W | BY |
| 4.0 | 9 | 5 | 6 | 1 | 9 | 5 | 6 | 1 | 9 | 5 | 6 | 3 |
| 2.0 | 9 | 5 | 7 | 0 | 9 | 5 | 7 | 0 | 9 | 3 | 7 | 0 |
| 1.0 | 9 | 3 | 6 | 0 | 9 | 0 | 5 | 0 | 9 | 3 | 6 | 0 |
| 0.5 | 9 | 0 | 5 | 0 | 9 | 0 | 5 | 0 | 9 | 1 | 5 | 0 |
| 0.25 | 9 | 0 | 3 | 0 | 8 | 0 | 0 | 0 | 8 | 0 | 3 | 0 |
| 0.125 | 6 | 0 | 1 | 0 | 6 | 0 | 0 | 0 | 7 | 0 | 1 | 0 |

I claim:

1. A solid, particulated herbicidal composition, comprising: a ternary molecular solution of from 10% to 30% by weight of octylphenoxy polyethoxy ethanol, 33% to 66% by weight of 1,2-dimethyl-3,5-diphenylpyrazolium salt and urea in amounts sufficient to adjust the weight of said composition to 100%; and wherein the above articulated herbicidal composition may optionally coated with a fumed synthetic silica or precipitated silica having a particle-size range of 0.015 micron to 2 microns and used in amounts of 1% to 5% by weight of said composition to be coated.

2. The composition according to claim 1, wherein the 1,2-dimethyl-3,5-diphenylpyrazolium salt is the 1,2-dimethyl-3,5-diphenylpyrazolium methylsulfate.

3. The composition according to claim 1, comprising 27% by weight of octylphenoxy polyethoxy ethanol; 64% by weight of 1,2-dimethyl-3,5-diphenylpyrazolium methylsulfate and 9% by weight of urea.

4. The composition according to claim 1, comprising 13.2% by weight of octylphenoxy polyethoxy ethanol; 33.4% by weight of 1,2-dimethyl-3,5-diphenylpyrazolium methylsulfate and 53.4% by weight of urea.

5. A method for the preparation of a solid herbicidal composition according to claim 1, comprising: heating 10% to 30% by weight of octylphenoxy polyethoxy ethanol to a temperature from 90° C. to 160° C., adding to and blending with it 33% to 66% by weight of 1,2-dimethyl-3,5-diphenylpyrazolium salt, and urea in amounts sufficient to adjust the weight of said composition to 100%; heating the resultant blend at a temperature range of from 90° C. to 160° C. for a period of time sufficient to obtain a homogeneous melt, and rapidly lowering the temperature of said melt until it congeals to a solid.

6. The method according to claim 5, wherein said pyrazolium salt is the 1,2-dimethyl-3,5-diphenylpyrazolium methylsulfate.

* * * * *